(12) United States Patent
Kim

(10) Patent No.: US 9,549,785 B2
(45) Date of Patent: Jan. 24, 2017

(54) METHOD OF MANUFACTURING GUIDE STENT OF DENTAL IMPLANT

(71) Applicant: DIO Corporation, Busan (KR)

(72) Inventor: Jin Chul Kim, Yangsan-si (KR)

(73) Assignee: DIO CORPORATION, Busan (KR)

( * ) Notice: Subject to any disclaimer, the term of this patent is extended or adjusted under 35 U.S.C. 154(b) by 54 days.

(21) Appl. No.: 14/565,471

(22) Filed: Dec. 10, 2014

(65) Prior Publication Data

US 2015/0265371 A1 Sep. 24, 2015

(30) Foreign Application Priority Data

Mar. 18, 2014 (KR) .......................... 10-2014-0031434

(51) Int. Cl.
| | | |
|---|---|---|
| *G06F 19/00* | (2011.01) | |
| *A61C 1/08* | (2006.01) | |
| *A61C 1/00* | (2006.01) | |
| *A61B 6/14* | (2006.01) | |
| *A61C 9/00* | (2006.01) | |
| *G06T 7/00* | (2006.01) | |

(52) U.S. Cl.
CPC ................ *A61C 1/084* (2013.01); *A61B 6/14* (2013.01); *A61C 1/0084* (2013.01); *A61C 9/004* (2013.01); *G06T 7/0028* (2013.01); *G06T 2207/10028* (2013.01); *G06T 2207/10081* (2013.01); *G06T 2207/30036* (2013.01)

(58) Field of Classification Search
CPC ....... A61C 1/0084; A61C 1/084; A61C 9/004; G06T 7/0028; G06T 2207/30036; G06T 2207/10028; G06T 2207/10081; A61B 6/14

USPC .................... 700/98; 433/29, 75; 702/167
See application file for complete search history.

(56) References Cited

U.S. PATENT DOCUMENTS

| | | | | |
|---|---|---|---|---|
| 2003/0219148 A1* | 11/2003 | Scharlack | .............. | A61C 1/084 382/128 |
| 2004/0029068 A1* | 2/2004 | Sachdeva | ................. | A61C 7/00 433/24 |
| 2009/0316966 A1* | 12/2009 | Marshall | .............. | A61B 6/5217 382/128 |
| 2010/0255445 A1 | 10/2010 | Gantes | | |

(Continued)

FOREIGN PATENT DOCUMENTS

| | | |
|---|---|---|
| KR | 10-0970341 B1 | 7/2010 |
| KR | 10-0990742 B1 | 10/2010 |
| KR | 10-1086865 B1 | 11/2011 |

*Primary Examiner* — Mohammad Ali
*Assistant Examiner* — Ziaul Karim
(74) *Attorney, Agent, or Firm* — Paratus Law Group, PLLC

(57) ABSTRACT

Disclosed is a method of manufacturing a guide stent of a dental implant. The method includes a first step of obtaining a three-dimensional image of periodontal tissue in a mouth of a patient through an CT scan and a three-dimensional exterior image corresponding to the three-dimensional image through an oral scan; a second step of matching the three-dimensional image and the three-dimensional exterior image through a difference amp which overlaps the three-dimensional image and the three-dimensional exterior image and outputs a matching degree between the images, and obtaining a three-dimensional procedure guide image; and a third step of manufacturing a stent body having a through hole corresponding to a preset implant implantation position according to the obtained three-dimensional procedure guide image.

1 Claim, 5 Drawing Sheets

(56) References Cited

U.S. PATENT DOCUMENTS

2011/0008751 A1* 1/2011 Pettersson .............. A61C 1/084
433/167
2014/0379356 A1* 12/2014 Sachdeva ............... A61C 7/002
705/2
2015/0209118 A1* 7/2015 Kopelman ............. A61B 19/54
433/25

* cited by examiner

-Prior Artary which was filed on Mar. 18, 2014,
METHOD OF MANUFACTURING GUIDE STENT OF DENTAL IMPLANT

CROSS-REFERENCE TO RELATED APPLICATION

This application claims the benefit of Korean Application No. 10-2014-31434 which was filed on Mar. 18, 2014, which is incorporated herein by reference in its entirety.

BACKGROUND

1. Field of the Invention

The present invention relates to a method of manufacturing a guide stent of a dental implant, and more particularly, to a method of manufacturing a guide stent of a dental implant, which is capable of diagnosing a dental implantation position according to obtained three-dimensional image information of periodontal tissue, guiding dental implantation in response to a diagnosed result, and improving surgical accuracy.

2. Discussion of Related Art

Generally, a dental implant is a implantation procedure in which a fixture formed of titanium or the like, so that the body does not react adversely, is implanted into an alveolar bone, from which a tooth falls out, so as to replace a lost tooth root, and then an artificial tooth is fixed thereto to restore a function of a tooth.

In the case of a prosthetic appliance or a denture, as time goes on, other teeth and bones therearound are eroded. However, the dental implant may prevent a damage of periodontal tissue therearound, and also may stably remove secondary dental caries production factors. Further, since the dental implant has the same structure as a natural tooth, there is no pain in the gums and feeling of irritation. Therefore, the dental implant has an advantage in that it may be semi-permanently used through continuous maintenance.

The dental implantation procedure is performed by forming a boring in the alveolar bone using a drill and then implanting the fixture in the boring. At this time, the forming of the boring and the implanting of the fixture may be different depending on a patient. This is because an implantation position, depth and direction of an implant should be determined in consideration of various factors such as a dental condition of a patient, a position of a tooth to be treated, and a condition of an alveolar bone of the patient.

Specifically, in a drilling operation for forming the boring in the alveolar bone, there is a problem in that it is very difficult for skilled operators as well as unskilled operators to precisely guess a drilling depth and direction during the operation. This is because it is not easy to determine a depth of the drilling operation when an operator performs the drilling operation by applying a force to the drill so as to form the boring in the alveolar bone, and also a nerve in the alveolar bone may be damaged when the drill is inserted over a certain depth.

In contrast, when the drilling operation is finished before reaching the certain depth, there may be some problems in which an excessive force due to a shallow boring depth may be exerted so as to fix the fixture, and also a screw thread around the boring may be damaged, or the fixture is not completely fixed, and thus a reoperation may be required.

Therefore, an assistant tool called a "guide stent" is used to find a precise position and direction in which the drilling operation is performed.

FIG. 1 is a flowchart illustrating a process of manufacturing a conventional guide stent.

As illustrated in FIG. 1, the conventional guide stent is manufactured in the following order. First, a female pattern of the periodontal tissue of a patient is obtained using a dental impression material formed of a rubber material (s1), and a plaster figure of the periodontal tissue of the patient is prepared by pouring plaster into the female pattern (s2).

Shapes of the tooth and the gum are obtained by a CT scan of the plaster figure (s2), and shapes of the alveolar bone and the tooth in the mouth are obtained by the CT scan on the patient (s3).

Then, the two images are matched with each other using a feature of the tooth or a feature of the plaster figure (s4). Further, a simulation is performed through image matched data, and a dental implant is planed (s5), and a guide stent capable of guiding the dental implant according to the plan is manufactured (s6).

At this time, the guide stent capable of guiding the dental implant should be manufactured by adding an operator's experience together with various anatomical conditions such as a thickness of the gum, a distribution of the alveolar bone, and a position of the target tooth of the patient. Therefore, it is more preferable to use exterior data of an oral organism than to use only direct data such as CT data.

To this end, a matching operation of matching each data with each other is essentially required. Conventionally, shape data of the plaster figure of the periodontal tissue in the mouth and the periodontal tissue data of the patient were matched based on the feature of the tooth. Alternatively, a method in which the plaster figure and a tray on which the plaster figure is seated are inserted into the mouth to obtain additional image data, and the image is matched based on a feature of the tray was used.

However, in the conventional image matching, since it takes an additional time to form the female pattern of the mouth shape of the patient and then to prepare the plaster model according to the female pattern, an entire operation time for the dental implant is increased. Further, since the female pattern and the plaster model corresponding to the patient should be prepared in every dental implantation procedure, an additional cost is generated, and thus economic efficiency in the dental implantation procedure is lowered.

Further, the image matching depends on accuracy of the plaster model. Therefore, in the case of the unskilled operator, accuracy of the image matching is lowered due to the low accuracy of the plaster model, and manufacturing ability irrelevant to medical ability is required. Furthermore, when the female pattern is manufactured, the accuracy of the female pattern is changed according to a biting force of the patient, elasticity of the gum, a tooth arrangement form and a tooth defect condition, and thus it is difficult to precisely and constantly manufacture the plaster model.

Therefore, the stent manufactured based on the inaccuracy plaster model is rough and unnecessarily thick. Thus, when the stent is inserted into the mouth of the patient, an opening angle of a jaw joint is increased, the jaw joint is strained and joint fatigue is increased, and also a space for the dental implantation procedure becomes narrow toward an inner side of the mouth, and thus difficulty in performing the dental implantation procedure is increased.

Further, since the accuracy of the guide stent is low, the fixture should be implanted into a previously formed boring, and high-priced custom abutment and crown (artificial tooth) should be manufactured according to a direction and an angle of the fixed fixture. Since the female pattern is obtained and then the custom abutment and the crown are designed, the number of hospital visits of the patient and a period of time until the dental implantation procedure is finished are increased.

SUMMARY OF THE INVENTION

According to an aspect of the present invention, there is provided a method of manufacturing a guide stent of a dental implant, including a first step of obtaining a three-dimensional image of periodontal tissue in a mouth of a patient through an CT scan and a three-dimensional exterior image corresponding to the three-dimensional image through an oral scan; a second step of matching the three-dimensional image and the three-dimensional exterior image through a difference amp which overlaps the three-dimensional image and the three-dimensional exterior image and outputs a matching degree between the images, and obtaining a three-dimensional procedure guide image; and a third step of manufacturing a stent body having a through hole corresponding to a preset implant implantation position according to the obtained three-dimensional procedure guide image.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
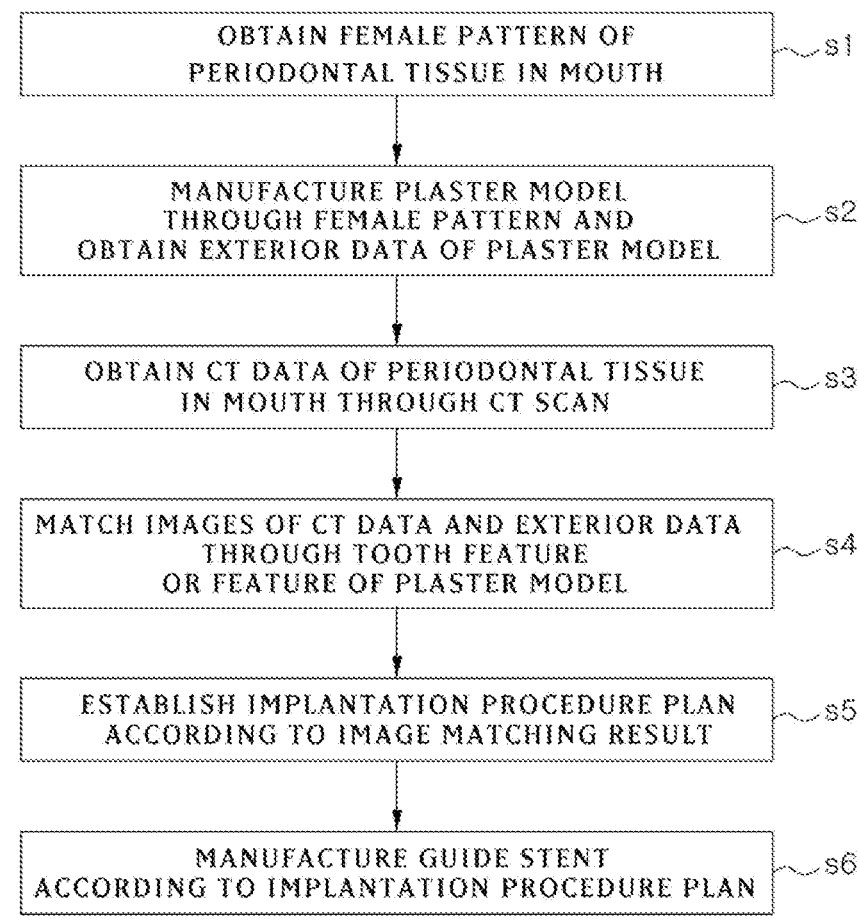
FIG. 1 is a flowchart illustrating a process of manufacturing a conventional guide stent.

Exemplary embodiments of the present invention will be described in detail below with reference to the accompanying drawings. In the embodiment, like reference numerals refer to like or corresponding elements regardless of reference numerals and a detailed description thereof will be omitted.

Hereinafter, a method of manufacturing a guide stent of a dental implant according to the present invention will be described in detail with reference to the accompanying drawings.

Figure 2:
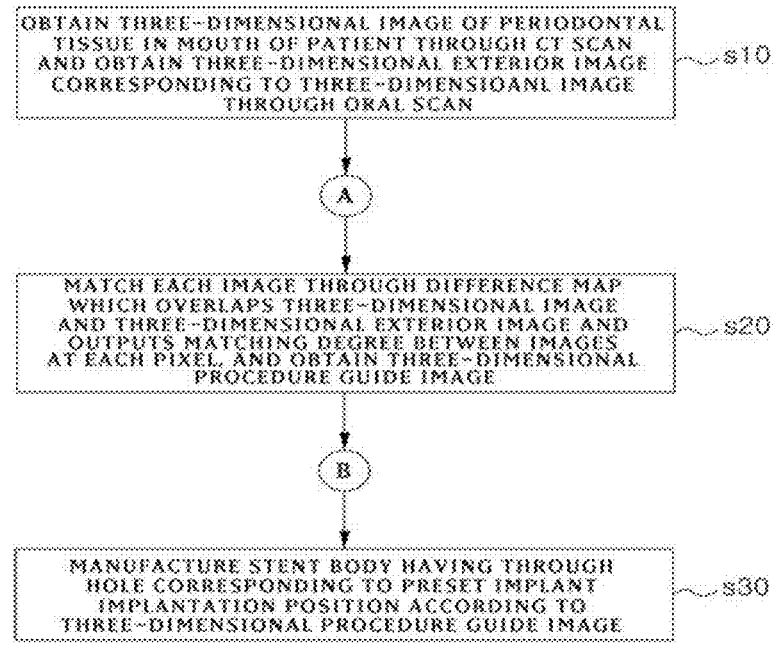
FIG. 2 is a flowchart illustrating a method of manufacturing a guide stent of a dental implant according to one embodiment of the present invention.
Figure 3:
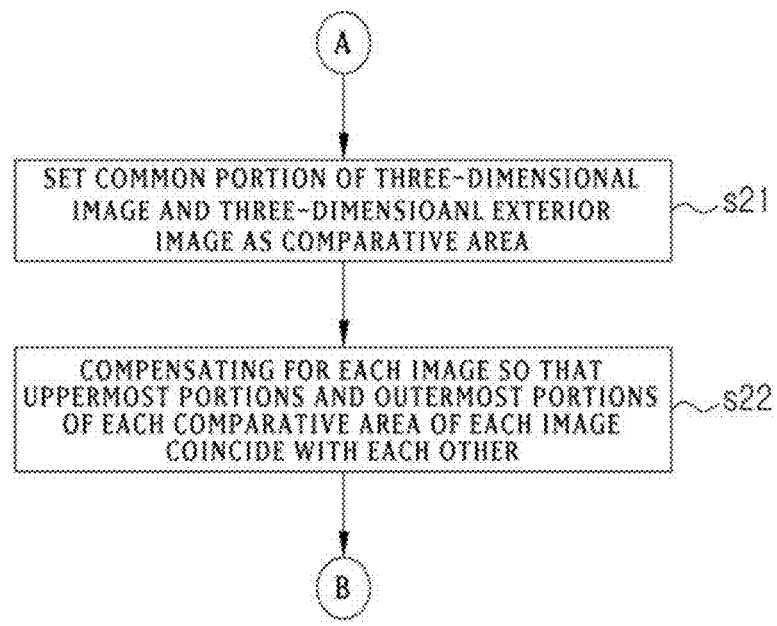
FIG. 3 is a flowchart illustrating an image matching method in the method of manufacturing the guide stent of the dental implant according to one embodiment of the present invention.
Figure 4A:
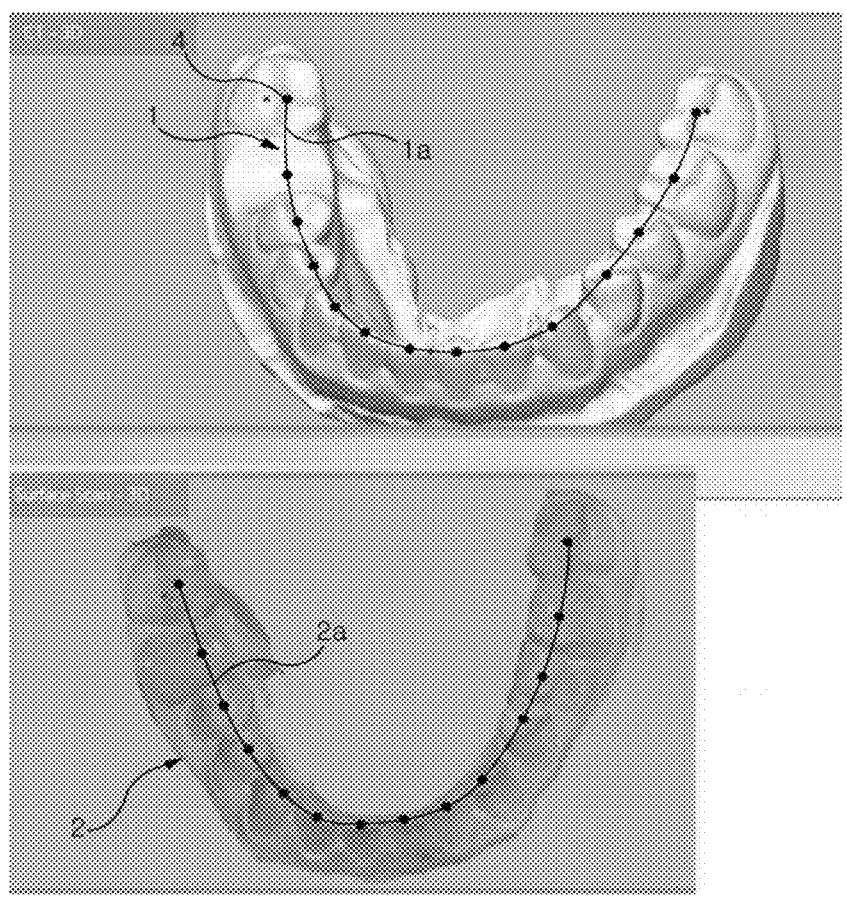
FIGS. 4A and 4B are exemplary views illustrating the image matching method in the method of manufacturing the guide stent of the dental implant according to one embodiment of the present invention.
Figure 4B:
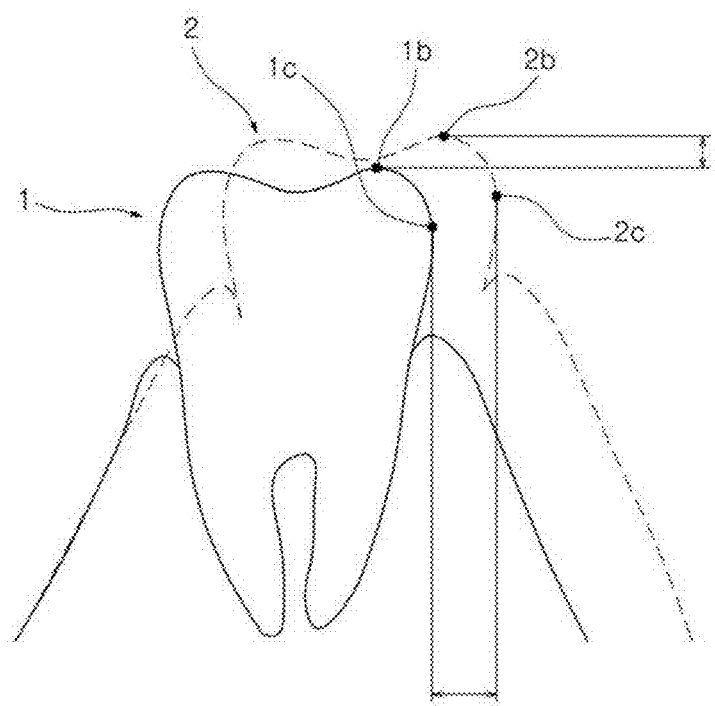
Figure 5:
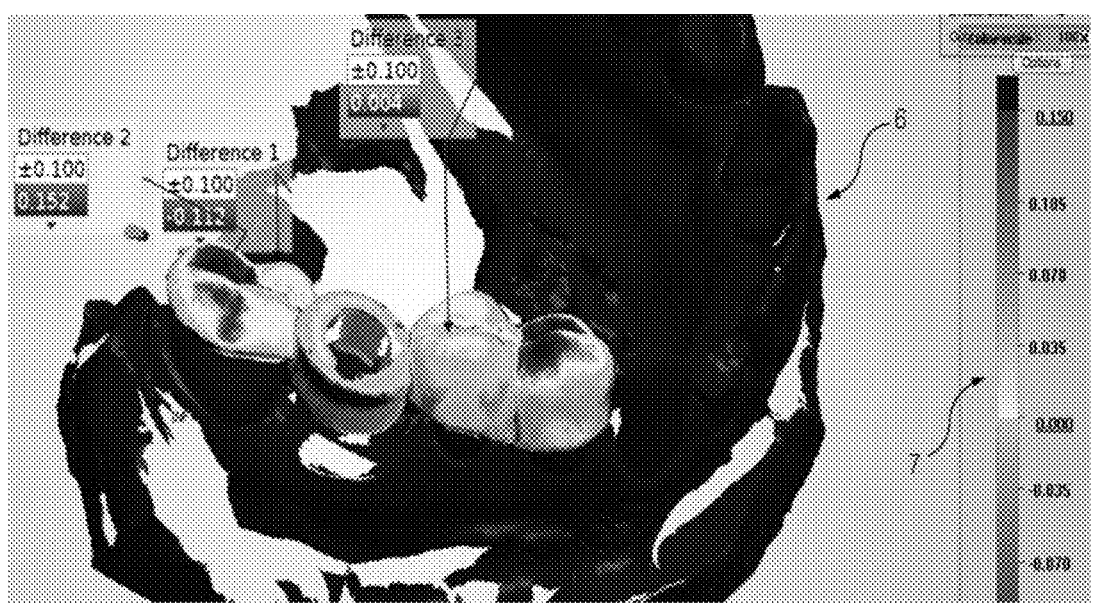
FIG. 5 is an exemplary view illustrating a difference map in the method of manufacturing the guide stent of the dental implant according to one embodiment of the present invention.
Figure 6:
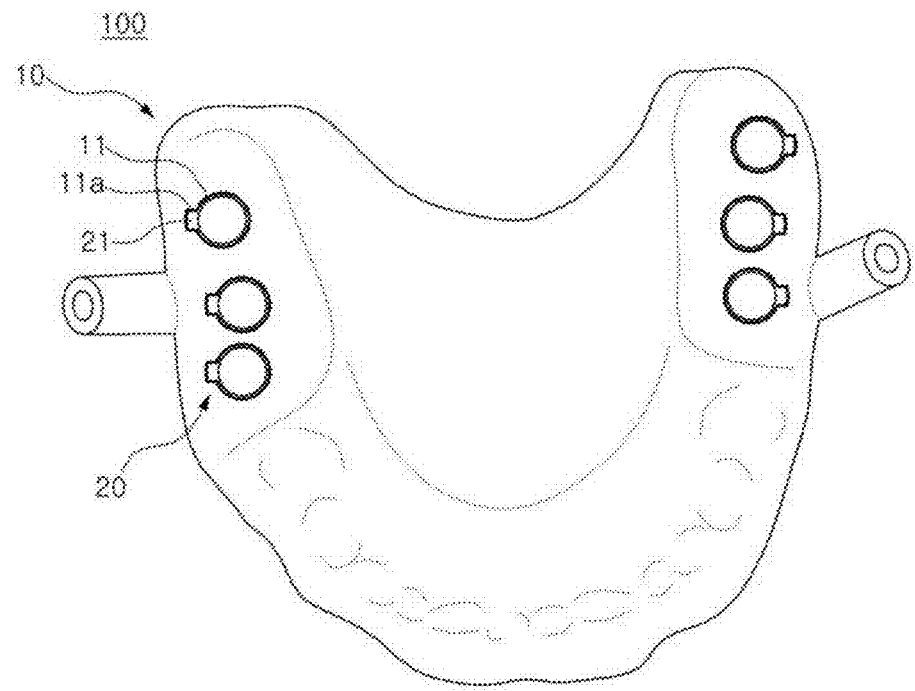
FIG. 6 is an exemplary view illustrating the guide stent of the dental implant manufactured according to one embodiment of the present invention.
Figure 7:
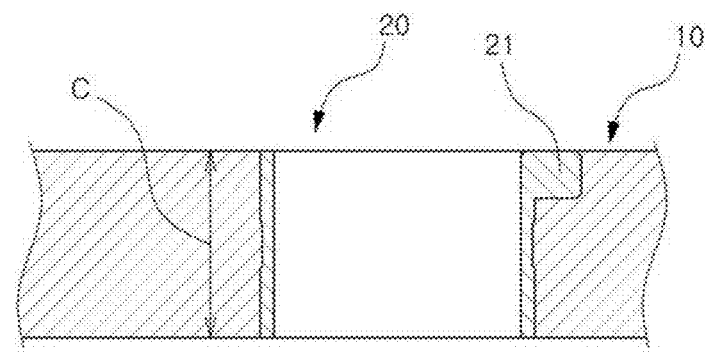
FIG. 7 is a cross-sectional view illustrating a main portion of the guide stent of the dental implant manufactured according to one embodiment of the present invention.

FIG. 2 is a flowchart illustrating the method of manufacturing the guide stent of the dental implant according to one embodiment of the present invention, FIG. 3 is a flowchart illustrating an image matching method in the method of manufacturing the guide stent of the dental implant according to one embodiment of the present invention, FIGS. 4A and 4B are exemplary views illustrating the image matching method in the method of manufacturing the guide stent of the dental implant according to one embodiment of the present invention, FIG. 5 is an exemplary view illustrating a difference map in the method of manufacturing the guide stent of the dental implant according to one embodiment of the present invention, FIG. 6 is an exemplary view illustrating the guide stent of the dental implant manufactured according to one embodiment of the present invention, and FIG. 7 is a cross-sectional view illustrating a main portion of the guide stent of the dental implant manufactured according to one embodiment of the present invention.

A dental implantation procedure is performed by forming a boring in a alveolar bone using a drill and then implanting the fixture in the boring, and an assistant tool called the guide stent is used to find a precise position and direction in which the drilling operation is performed.

Here, the guide stent 100 is manufactured to guide an established implantation plan, when the implantation plan is established according to a condition of periodontal tissue in a mouth of a patient, and thus to guide a direction, a depth or the like of the drilling or the implanting of the fixture.

As illustrated in FIGS. 2 to 7, the method of manufacturing the guide stent of the dental implant according to one embodiment of the present invention is performed as follows.

First, a three-dimensional image 1 of the periodontal tissue in the mouth through a CT scan and a three-dimensional exterior image 2 corresponding to the three-dimensional image 1 through an oral scan are obtained (s10).

For example, the three-dimensional image 1 is obtained through the CT scan or the like, and includes information of a crown (an upper side of a tooth exposed to an outer side of the gum) of the periodontal tissue in the mouth, a tooth root (a lower side of the tooth located at an inner side of the gum and coupled to the alveolar bone), and internal tissue such as the alveolar bone. That is, information of the tooth and the alveolar bone may be provided clearly, but information of the gum may not be provided clearly.

However, the three-dimensional exterior image 2 is obtained by the oral scan, and includes a shape of the gum around the tooth root of the periodontal tissue in the mouth, which is not provided clearly on the three-dimensional image. That is, the information of the crown of the tooth and the gum may be provided clearly, but the information of the tooth root in the gum and the alveolar bone is may not be provided clearly.

The dental implantation procedure should consider internal conditions and external conditions such as arrangement and engagement between the alveolar bone and the fixture according to a bone mass, a bone density and a distribution of the alveolar bone, a space between the teeth, and an exterior and an arrangement angle of the crown (artificial tooth). Therefore, it is possible to provide a high quality dental implantation procedure when synthetically using both of the three-dimensional image 1 and the three-dimensional exterior image 2, compared with when using only one of them.

At this time, since it is not required to prepare the separate plaster figure when the exterior shape of the periodontal tissue in the mouth of the patient is obtained, a preparing time for the dental implantation procedure is reduced, and thus the number of hospital visits of the patient may be reduced, and satisfaction in the dental implantation procedure may be also enhanced.

Further, instead of matching the three-dimensional image 1 through the CT scan with the exterior image of the inaccurate plaster figure, the information of the periodontal tissue in the mouth through the CT scan is matched with the three-dimensional exterior image 2 obtained by directly scanning the mouth of the patient to obtain a more accurate image matching result, and thus the guide stent may be more accurately manufactured.

The guide stent is more accurately manufactured by reflecting an accurate diagnosis and a more precise implant design, and thus the dental implantation procedure may be precisely performed without any compensation of the implantation procedure plan through obtaining of an additional impression in a crown coupling operation or an abutment implanting operation after the fixture is implanted.

Therefore, by manufacturing the custom abutment and the crown together with the guide stent, it is possible to provide a generic technology device which may complete the implanting of the fixture and the installing of the abutment/crown at only one implantation procedure, after the guide stent is manufactured.

Meanwhile, the three-dimensional image and the three-dimensional exterior image are obtained (s10). Then, the three-dimensional image and the three-dimensional exterior image are matched with each other through a difference map 6 which overlaps the three-dimensional image and the three-dimensional exterior image and outputs a matching degree between the images at each pixel, and thus a three-dimensional procedure guide image is obtained (s20).

Here, the information of the periodontal tissue in the mouth of the patient is converted into three-dimensional vector data by a CT scanner or an oral scanner, and thus the three-dimensional image 1 and the three-dimensional exterior image 2 may be formed and obtained.

And the three-dimensional vector data of each image may be digitalized and then stored in a storage device of a computer, and an image processing process for overlapping each image may be performed based on the computer.

At this time, the information of the periodontal tissue included in the three-dimensional image 1 and the information of the periodontal tissue included in the three-dimensional exterior image 2 may be combined through the image processing process. That is, by combining the shape information of the alveolar bone and the tooth root in the gum with the shape of the gum around the tooth root, it is possible to provide synthetic information for the dental implantation procedure.

In other words, the image matching of the three-dimensional image 1 and the three-dimensional exterior image 2 means that the two images are combined based on the crown which is commonly shown in the two images. That is, this may be understood as a meaning that the information of the gum coupled to the tooth root and the alveolar bone is matched with the information of the tooth root and the alveolar bone connected with the crown.

Here, the matching degree indicates a degree of similarity between the three-dimensional image 1 and the three-dimensional exterior image 2 as a matching error between the two images. As an absolute value of the matching error becomes low, it means that the two images are matched with each other and accurately overlapped, and it may be said that the matching degree is high.

And as the absolute value of the matching error becomes high, it means that the two images are inaccurately overlapped and dislocated from each other, and it may be said that the matching degree is low. That is, when the matching error is 0, the matching degree is the highest. It may be said that the matching degree is lowered in proportion to the absolute value of the matching error.

For example, when the three-dimensional image and the three-dimensional exterior image are overlapped, the matching degree may indicate such a degree that a surface of one image protrudes or is recessed from a surface of the other image.

At this time, the matching degree may be calculated through the three-dimensional vector data of each image. For example, the three-dimensional vector data of each image may be converted into the same coordinate system, and height information of the surface in each image may be numerically indicated through the three-dimensional vector data converted into the same coordinate system.

And the extent that the surface of one image protrudes or is recessed from the surface of the other image may be calculated at each portion of the overlapped images by comparing the surface heights of the overlapped images. That is, when the extent that the surface of one image protrudes or is recessed from the surface of the other image is large, it means that the absolute value of the matching error is larger, and the matching degree is low.

At this time, when the surface of one image protrudes more than the surface of the other image, the matching error has a positive value, and when the surface of one image is recessed more than the surface of the other image, the matching error has a negative value.

And the difference map 6 is formed by overlapping each image, and the matching degree is displayed at each pixel. That is, the difference map 6 includes all of the information of the three-dimensional image 1 and the information of the three-dimensional exterior image 2, and displays the matching degree between the overlapped images at each pixel.

At this time, the image matching for enhancing the matching degree displayed at each pixel of the difference map 6 is performed and then completed. Then, the three-dimensional procedure guide image including all of the information of the three-dimensional image 1 and the information of the three-dimensional exterior image 2 may be obtained by removing a layer in which the matching degree is displayed.

And the guide stent which guides the dental implantation procedure may be manufactured through the obtained three-dimensional procedure guide image, and the prosthetic appliance such as the custom abutment and the crown, which is necessary in the dental implantation procedure, may be manufactured.

At this time, the obtaining of the three-dimensional procedure guide image through the difference map 6 may be achieved by a simulation program based on the computer using the digitalized three-dimensional image 1 and three-dimensional exterior image 2.

Through the simulation program, a prosthetic result, such as tooth occlusion and an exterior shape of the tooth, after the dental implantation procedure may be estimated by associating with the obtaining of the three-dimensional procedure guide image. Therefore, the higher quality dental implantation procedure may be provided by sharing the estimated result with the patient and a dental technician who manufactures the corresponding prosthetic appliance.

Further, since a more precise procedure plan may be established through the three-dimensional procedure guide image, a separate re-measuring process is not required in every stage of the dental implantation procedure, such as forming of the boring, implanting of the fixture, manufacturing and implanting of the custom abutment, and manufacturing and implanting of the crown.

Therefore, since various prosthetic appliances necessary in the follow-up procedures may be manufactured with the guide stent, the number of hospital visits of the patient and the period of time for the dental implantation procedure may be considerably reduced. Further, the generic technology device for one day dental implantation, which may complete the implanting of the fixture and the installing of the abutment/crown at only one implantation procedure, may be provided.

The prosthetic result estimated by the simulation program may be stored in the form of data which is compatible with CAD/CAM manufacturing equipment or the like. Thus, in the case of a simple prosthetic appliance, it may be immediately manufactured by the manufacturing equipment together with the calculation of the prosthetic result.

Meanwhile, if the three-dimensional procedure guide image is obtained (s20), a stent body having a through hole corresponding to a preset implant implantation position according to the obtained three-dimensional procedure guide image is manufactured (s30).

A tooth arrangement and a tooth defect position of the patient, a shape and a bone density of the alveolar bone to which the tooth is coupled, and a gum condition covering the alveolar bone and the tooth root may be fully indicated in the three-dimensional procedure guide image.

Therefore, the operator may obtain detailed and precise information including a visible exterior shape of the defect position of the tooth to be treated, and internal tissue corresponding to this.

That is, the operator may determine an implantation position of the fixture in the implant implantation position, and also may determine the direction and the depth of the boring according to the shape and the bone density of the alveolar bone.

Of course, the above-mentioned simulation system may be used in the implant diagnosis and the implantation procedure plan. At this time, the simulation system may calculate all information relevant to the dental implantation procedure, such as a binding force of the fixture according to the direction and the depth of the boring, and whether the fixture or the alveolar bone may withstand a pressure required when chewing with teeth, and then may provide the information to the operator.

At this time, an internal profile of the stent body 10 may be formed in an external profile of the periodontal tissue in the mouth of the patient indicated in the three-dimensional procedure guide image. The profiles may be mutually combined and then matched and coupled with the tooth of the patient.

The through hole 11 is disposed at a position in which the boring will be formed, while the stent body 10 is coupled in the mouth of the patient, and a direction of the through hole 11 may be determined according to the direction of the boring. Further, the external profile such as a thickness and a shape around the through hole may be determined so that the stent body 10 guides the depth of the boring.

Here, the stent body 10 may be designed based on the three-dimensional procedure guide image. For example, when the three-dimensional procedure guide image is input, the simulation system may calculates an inner surface profile of the stent body 10 in which the exterior shape of the periodontal tissue in the mouth of the patient is inserted.

A position and a direction of the through hole 11 may be calculated by an input of the operator or an internal algorithm. Further, the external profile of the stent body 10 may be provided to have a thickness which protects teeth during the dental implantation procedure and also to have a similar shape to the internal profile. The external profile around the through hole 11 may be provided to have a thickness or a shape which may support the drill or may guide a depth of the drill.

At this time, if a design of the stent body 10 is determined according to the calculated result, information of coordinates or an image of a three-dimensional shape of the design is input to the manufacturing equipment, and then the stent body 10 may be manufactured. Here, the manufacturing equipment may be a precise CNC machine, a 3D printer or the like, and a complete product corresponding to the input three-dimensional coordinates or the three-dimensional image information may be manufactured.

Meanwhile, referring to FIGS. 3 and 4a, the operation s20 of obtaining the three-dimensional procedure guide image may include an operation s21 of setting a common portion of the three-dimensional image 1 and the three-dimensional exterior image 2 as a comparative area, and an operation s22 of compensating for each image so that the uppermost portions 1b and 2b and the outermost portions 1c and 2c of each comparative area coincide with each other in the overlapped three-dimensional image 1 and three-dimensional exterior image 2.

Here, in the overlapped three-dimensional image 1 and three-dimensional exterior image 2, the three-dimensional exterior image 2 may be compensated, based on the three-dimensional image 1, such that the uppermost portions 1b and 2b and the outermost portions 1c and 2c coincide with each other.

Specifically, the three-dimensional image 1 may be obtained through the CT scanner, and includes the information of the crown, the tooth root and the alveolar bone of the tooth formed by combining radiation tomography images.

Further, the three-dimensional exterior image 2 may be obtained through the oral scanner, and may include the information of the crown of the tooth and the gum formed by obtaining and combining the scan images along the periodontal tissue in the mouth of the patient.

As described above, the three-dimensional image 1 and the three-dimensional exterior image 2 include common information of the crown of the tooth, and thus the three-dimensional image 1 and the three-dimensional exterior image 2 may be matched with each other based on the common information.

At this time, an area indicating the crown which is the common portion of each image may be set as the comparative area. An operation of calculating the common portion at each image and setting the common portion as the comparative area may be automatically performed by an image processing device, and also the operator may manually set the comparative area.

Meanwhile, the three-dimensional exterior image 2 may be obtained by the oral scan. At this time, the oral scan may be performed using an oral scanner or the like. While the upper and lower teeth of the patient bite each other, a scanning is performed along a narrow surface of a molar tooth (a back tooth) and a labial surface (a lip side) of a front tooth (a canine tooth and a front tooth), and while the upper and lower teeth of the patient are parted, the scanning is performed along a cutting plane of a tooth.

And in the image information processing device of the oral scanner, the scanned image information is combined with the three-dimensional exterior image 2 including the entire shape of the crown of the tooth and the gum.

Here, since the three-dimensional exterior image 2 is obtained by combining image information continuously taken by the oral scanner moving in the mouth of the patient, a curvature of a tooth arrangement indicated in the combined three-dimensional exterior image 2 may be indicated to be distorted compared with the actual periodontal tissue.

That is, the three-dimensional exterior image 2 may have an image which is more broadened from the front tooth toward the back tooth side or more bent up and down than the curvature of the tooth arrangement of the actual periodontal tissue. The distortion of the tooth arrangement may occur during a combining process of the scanned image.

At this time, information of a width, a volume or the like of each tooth in the three-dimensional exterior image 2 precisely indicates information of the actual periodontal tissue. Therefore, the three-dimensional exterior image 2 may be compensated to have the accurate curvature of the tooth arrangement, and may be combined with the three-dimensional procedure guide image, and thus an accurate image matching result may be obtained.

Here, referring to FIG. 4B, each image may be compensated and matched in the overlapped three-dimensional image 1 and three-dimensional exterior image 2 so that the uppermost portions 1b and 2b and the outermost portions 1c and 2c of the comparative area coincide with each other (s22).

And in the overlapped three-dimensional image 1 and three-dimensional exterior image 2, the curvature of the tooth arrangement of the three-dimensional exterior image 2 may be compensated based on the curvature of the tooth arrangement indicated in the three-dimensional image 1. Through such a process, the matching result coinciding with the curvature of the tooth arrangement of the actual periodontal tissue may be obtained.

At this time, the three-dimensional exterior image 2 is moved vertically or horizontally, such that the uppermost portion 2b and the outermost portion 2c of the crown of the three-dimensional exterior image 2 coincide with the uppermost portion 1b and the outermost portion 1c of the crown of the three-dimensional image 1, and thus the curvature of the tooth arrangement of the three-dimensional exterior image 2 may be compensated.

Here, the horizontal and vertical movement of the three-dimensional exterior image 2 may be achieved through movement of each cross section of the image arranged along the tooth arrangement by a three-dimensional rendering method and an interpolation between the cross sections.

As described above, even though a separate oral insert, in which a reference point for the image matching is indicated, is not inserted into the mouth, the information of each image may be integrated and matched into the three-dimensional procedure guide image. Therefore, part of the periodontal tissue is not hidden by the tray, and the precise and accurate image may be obtained, and also the operation of obtaining and compensating for the additional image of the hidden periodontal tissue may be removed, and thus an image processing speed may be increased.

Meanwhile, the operation s21 of setting the comparative area may include an operation of dividing and outputting the matching degree between the images with each color, and an operation of designating and inputting a portion, of which the matching degree is lower than a preset matching degree in the comparative area, as an error area.

Here, the matching degree between the overlapped three-dimensional image 1 and three-dimensional exterior image 2 is indicated in each pixel of the difference map 6. The matching degree may be indicated as the matching error between the overlapped images in each pixel.

Here, the matching error between the overlapped images in each pixel of the difference map 6 is indicated by colors so that the operator may easily recognize an image matching process and may intuitionally determine accuracy of the image matching result.

For example, referring to a color table 7 for each matching error of FIG. 5, a portion in which a surface of the three-dimensional exterior image 2 protrudes to an outer side of a surface of the three-dimensional image 1 is indicated by a red color, and a portion in which the surface of the three-dimensional exterior image 2 is recessed into the surface of the three-dimensional image 1 is indicated by a blue color, and a portion in which the three-dimensional image 1 and the three-dimensional exterior image 2 are matched with each other is indicated by a green color.

Through the colors, the operator may easily determinate whether an important portion in the dental implantation procedure is accurately matched, even after the image matching process. If the essential portion in the dental implantation procedure is not accurately matched, a re-matching process or a compensating process is performed to obtain a more precise matching image.

The portion of which the matching degree is lower than the preset matching degree in the comparative area means a portion having the matching error larger than a predetermined value which has a great effect on a completeness of the three-dimensional procedure guide image, or which is difficult to be compensated.

Therefore, instead of calculating the entire difference map at a time, and the three-dimensional exterior image 2 is compensated, the operator intuitionally determines the accuracy of the image matching result through the matching degree which is divided and output by each color. And through the immediate determination of the accuracy of the important portion in the dental implantation procedure, an area having a large error may be set in the difference map, and the compensation may be performed in only the set area, and thus the image calculation process may be performed rapidly.

As an example of an image matching method, the operation s22 of compensating for the three-dimensional exterior image 2 may include an operation of dividing the difference map 6 within the error area into a plurality of cross sections along a curve of the tooth arrangement, and an operation of parallelly moving the three-dimensional exterior image 2 up and down and left and right and compensating for the curve of the tooth arrangement so that the uppermost portions and the outermost portions of each comparative area coincide with each other in each of the divided cross sections.

At this time, the curve 1a, 2a of the tooth arrangement means a curve representing the image of the crown set as the comparative area in each image. For example, if a center point of each tooth is set as a representative point 4, a U-shaped curve of the tooth arrangement may be formed along the representative points.

Here, when the information of the crown and the gum is restored three-dimensionally based on the curve of the tooth arrangement, the three-dimensional exterior image 2 may be obtained, and when the information of the crown, the tooth root and the alveolar bone is restored three-dimensionally based on the curve of the tooth arrangement, the three-dimensional image 1 may be obtained.

And when each curve of the tooth arrangement is aligned, and all of the information of the crown, the gum, the tooth root and the alveolar bone is restored, the three-dimensional procedure guide image may be obtained.

That is, the curves 1a and 2a of the tooth arrangement may be indicated by connecting the representative point 4 of the crowns of each tooth in each image. At this time, the representative points 4 of the crowns in each image may coincide with each other by coinciding the uppermost portions 1b and 2b and the outermost portions 1c and 2c of the crowns in each image with each other, and thus the curve of the tooth arrangement formed by connecting the representative points may be compensated.

And the three-dimensional image and the three-dimensional exterior image may be matched with each other through the compensated curve of the tooth arrangement, and thus the three-dimensional procedure guide image may be obtained.

Here, the difference map 6 within the error area may be divided into a plurality of cross sections including one point in the curve of the tooth arrangement. For example, one cross section may be formed at each representative point, and the curve of the tooth arrangement may be divided into segmentalized points, and then one cross section may be formed at each point.

At this time, the shape information of the crown, the tooth root and the alveolar bone in the three-dimensional image 1 and the shape information of the crown and the gum in the three-dimensional exterior image 2 are indicated at each cross section.

The parallel movement may be performed so that the crown in the three-dimensional image 1 coincides with the crown in the three-dimensional exterior image 2, and thus the curve of the tooth arrangement may be compensated. At this time, the three-dimensional exterior image 2 in each cross section is parallelly moved up and down so that the uppermost portion of the crown in the three-dimensional image 1 coincides with the uppermost portion of the crown in the three-dimensional exterior image 2. Further, the three-dimensional exterior image 2 in each cross section is parallelly moved left and right so that the outermost portion of the crown in the three-dimensional image 1 coincides with the outermost portion of the crown in the three-dimensional exterior image 2, and thus the two image may be matched with each other.

Of course, the above-mentioned image matching method is only one example, the difference images may be matched with each other in various methods using the reference point for the image matching.

Meanwhile, referring to FIGS. 6 and 7, the operation s30 of manufacturing the stent body 10 according to the obtained three-dimensional procedure guide image may include an operation of forming a matching groove, in which the periodontal tissue in the mouth of the patient is inserted and fixed, in the stent body 10, and an operation of designing the crown according to the three-dimensional procedure guide image and establishing a fixture implantation guide angle of the through hole 11 to correspond to an arrangement angle of the designed crown.

Here, the stent body 10 serves to guide the drilling in a state which is fixed to the periodontal tissue in the mouth of the patient. At this time, the matching groove is formed at a contact portion between the stent body 10 and the periodontal tissue. As the periodontal tissue is inserted into the matching groove, the stent body 10 may be fixed to the periodontal tissue.

Further, a guide groove 11a configured to guide the fixture implantation angle may be provided at the through hole 11. Of course, a sleeve 20 formed of a brass material may be provided at the through hole 11 to reduce friction generated during the drilling operation. The sleeve 20 may be coupled by inserting a guide protrusion 21 formed along an outer circumferential surface thereof into the guide groove 11a.

Specifically, the crown is coupled to an end of the abutment coupled to the fixture. And a coupling part between the fixture and the abutment and a coupling part between the abutment and the crown may be formed in a honeycomb shape not to be damaged by a pressure applied when chewing with teeth, and may be coupled to be in completely close contact with each other in only a preset direction.

Here, the implantation guide angle means an angle in which the guide groove 11a is formed at the through hole 11. The fixture may be inserted and implanted according to the arrangement angle of the previously designed crown by aligning the guide groove 11a with the reference point formed at one side of the fixture.

When the three-dimensional procedure guide image is obtained, the guide groove 11a may be formed so as to guide a coupling angle between the abutment and the fixture according to the arrangement angle in which the crown to be used as an artificial tooth is coupled in the mouth.

That is, if the abutment to which the crown is coupled and the fixture to which the abutment is coupled are aligned with each other based on the guide groove, the crown may be coupled in the mouth so as to suit the implantation procedure plan designed according to the three-dimensional procedure guide image.

Therefore, since the crown may be manufactured together with the guide stent 100 at the time at which the three-dimensional procedure guide image is obtained, the period of time for the dental implantation procedure may be considerably reduced.

That is, instead of manufacturing the crown to correspond to an angle in which the fixture is implanted, the crown may be manufactured so that an arrangement angle of the crown is established when the guide stent 100 is manufactured. Therefore, a period of time for preparing the dental implantation procedure and manufacturing various prosthetic appliances may be remarkably reduced, and also it is possible to provide the generic technology device which may complete removing of the gum, drilling of the boring for the fixture implantation, implanting of the fixture and the installing of the abutment/crown at only one implantation procedure.

The stent body 10 has a constant thickness c to support a drill or to guide an up and down movement of the drill. At this time, the through hole 11 may rotatably support an outer circumference of the drill and may guide the up and down movement thereof.

Of course, when the sleeve 20 is inserted into the through hole 11, the guide hole formed in the sleeve 20 serves as the through hole, and the description of the through hole which will be described later may be equally applied to the guide hole.

Here, the through hole 11 is formed to include an additional diameter which may control an insertion direction of the drill, and thus, when an error between a boring forming direction and a direction of the through hole 11 is generated due to a coupling error between the stent body 10 and the periodontal tissue, the error may be compensated. Therefore, due to the additional diameter, the through hole 11 should be formed to have a deep depth and to stably guide the up and down movement of the drill.

At this time, since the stent body of the present invention is manufactured by obtaining the exterior shape information of the periodontal tissue from the three-dimensional exterior image directly obtained through the oral scan, instead of the inaccurate plaster model, the stent body 10 may be manufactured to be more precisely matched with the periodontal tissue.

Therefore, the error between the boring forming direction and the direction of the through hole 11 is not generated, and the additional diameter for controlling the insertion direction of the drill may be removed, and thus the stent body may be formed so that the through hole 11 is substantially matched with an outer diameter of the drill. At this time, the terms "substantially matched" may be interpreted as a meaning that the through hole includes a minimum space for rotation of the inserted drill.

That is, since the through hole may be in more tightly close contact with the outer diameter of the drill, the drill may be stably guided, even though the depth of the through hole is reduced. Further, vibration generation due to a space between the through hole and the drill may be considerably reduced, and thus the thickness for protecting the periodontal tissue of the patient may be reduced.

The dental implantation procedure is performed while the guide stent is inserted into the mouth of the patient. It has been known that, even though a difference in the thickness of the stent body was very slight, it had a large effect on a difference in the feeling of irritation of the patient according to the thickness of the stent body.

The stent body may is provided to have a minimum thickness by such a precise design, and the thickness from the alveolar bone to a surface of the stent may be 9 mm or less. Therefore, when the stent is inserted into the mouth, an opening angle of a jaw joint may be reduced, and thus the feeling of irritation and the joint fatigue due to the opening of the jaw joint may be remarkably reduced, and the satisfaction in the dental implantation procedure may be also enhanced. Furthermore, a space which may be used in the dental implantation procedure is increased in a limited space of the mouth, and thus the dental implantation procedure may be accurately and stably performed, and the completeness of the dental implantation procedure may be increased.

Accordingly, the present invention provides the following effects.

First, since it is not required to manufacture the separate plaster figure when the exterior shape of the periodontal tissue in the mouth of the patient is obtained, the period of time for preparing the dental implantation procedure can be reduced, and the number of hospital visits of the patient can be reduced, and the satisfaction in the dental implantation procedure can be enhanced. Therefore, the three-dimensional image obtained through the CT scanning is matched with the three-dimensional exterior image obtained by directly scanning the mouth of the patient, instead of the exterior image of the inaccurate plaster figure, and the more precise image matching operation can be performed. Based on this, the result corresponding to an actual condition can be obtained, and thus the precise guide stent can be manufactured.

Second, the accurate and precise three-dimensional procedure guide image and the implantation procedure plan can be established based on the three-dimensional exterior image obtained by directly scanning the mouth of the patient. Therefore, the separate re-measuring process is not required in every stage of the dental implantation procedure, such as the forming of the boring, the implanting of the fixture, the manufacturing and implanting of the custom abutment, and manufacturing and implanting of the crown. And since the various prosthetic appliances necessary in the follow-up procedures can be manufactured together with the guide stent, it is possible to provide the generic technology device which can complete the implanting of the fixture and the installing of the abutment/crown at only one implantation procedure.

Third, even though the separate mouth insert which provides an image matching point is not provided, each image can be compensated and matched according to the matching degree of the difference map, and thus the accurate image of the periodontal tissue, which is not damaged by the mouth insert, can be obtained. Therefore, the more precise guide stent can be manufactured, and the feeling of irritation of the patient due to the mouth insert is removed, and the satisfaction in the dental implantation procedure can be also enhanced.

Fourth, since the difference map divides and outputs the matching degree between the images with each color, the operator can intuitively determine the accuracy of the image matching result. And through the immediate determination of the accuracy of the important portion in the dental implantation procedure, the area having the large error can be set in the difference map, and the compensation can be performed in only the set area, and thus the image calculation process can be performed rapidly. Further, a follow-up compensating operation for obtaining the precise three-dimensional procedure guide image can be smoothly performed.

Fifth, since the thickness of the stent body from the surface of the alveolar bone to the surface of the stent body can be formed as thin as possible through the precise design, the opening angle of the jaw joint can be reduced when the stent body is inserted into the mouth of the patient, the feeling of irritation and the joint fatigue due to the opening of the jaw joint can be remarkably reduced, and the satisfaction in the dental implantation procedure can be enhanced. Furthermore, the space which can be used in the dental implantation procedure is increased in the limited space of the mouth, and thus the dental implantation procedure can be accurately and stably performed, and the completeness of the dental implantation procedure can be increased.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A method of manufacturing a guide stent of a dental implant, comprising:
   obtaining a three-dimensional image of periodontal tissue in a mouth of a patient through a computerized tomography (CT) scan by a CT scanner and a three-dimensional exterior image of an inside of the mouth of the patient through an oral scan by an oral scanner;
   displaying on a display screen a difference map, including overlapping the three-dimensional image and the three-dimensional exterior image, matching a common portion of the three-dimensional image and the three-dimensional exterior image, and displaying a matching degree on the overlapped images displayed on the display screen with a first color on a first area where an outline of the three-dimensional exterior image protrudes with respect to an outline of the three-dimensional image, a second color on a second area where the outline of the three-dimensional exterior image is recessed with respect to the outline of the three-dimensional image, and a third color on a third area where the three-dimensional exterior image and the three-dimensional image are matched with each other;

obtaining a three-dimensional procedure guide image by image calculation processing using a hardware image processing processor, including setting on the difference map an error area where the matching degree in the difference map is lower than a preset matching degree, and amending the error area such that outlines of the three-dimensional image and the three-dimensional exterior image positioned within the error area coincide with each other, wherein the amending the error area includes:

dividing the error area into a plurality of cross sections along a curve of a tooth arrangement, and moving the outline of the three-dimensional exterior image to coincide with the outline of the three-dimensional image, in each cross section of the plurality of cross sections; and manufacturing a stent body having a through hole corresponding to a preset implant implantation position according to the obtained three-dimensional procedure guide image, wherein the manufacturing the stent body comprises forming a matching groove, in which the periodontal tissue in the mouth of the patient is inserted and fixed, in the stent body, and designing a crown according to the three-dimensional procedure guide image and establishing a fixture implantation guide angle of the through hole to correspond to an arrangement angle of the designed crown.

* * * * *